United States Patent
Ichim et al.

(10) Patent No.: US 10,792,305 B2
(45) Date of Patent: Oct. 6, 2020

(54) THERAPEUTIC IMMUNE MODULATION USING NOBLE GAS COMPOSITIONS

(71) Applicant: NOBILIS THERAPEUTICS, INC., Portland, OR (US)

(72) Inventors: Thomas Ichim, San Diego, CA (US); Vlad Bogin, Portland, OR (US)

(73) Assignee: Nobilis Therapeutics, Inc., Portland, OR (US)

( * ) Notice: Subject to any disclaimer, the term of this patent is extended or adjusted under 35 U.S.C. 154(b) by 0 days.

(21) Appl. No.: 15/738,025

(22) PCT Filed: Jun. 23, 2016

(86) PCT No.: PCT/US2016/039038
§ 371 (c)(1),
(2) Date: Dec. 19, 2017

(87) PCT Pub. No.: WO2016/210144
PCT Pub. Date: Dec. 29, 2016

(65) Prior Publication Data
US 2018/0303871 A1      Oct. 25, 2018

Related U.S. Application Data

(60) Provisional application No. 62/183,624, filed on Jun. 23, 2015, provisional application No. 62/276,753, filed on Jan. 8, 2016.

(51) Int. Cl.
*A61K 33/00* (2006.01)
*A61K 9/00* (2006.01)
(Continued)

(52) U.S. Cl.
CPC ............ *A61K 33/00* (2013.01); *A61K 9/0073* (2013.01); *A61P 25/28* (2018.01); *G01N 33/6863* (2013.01)

(58) Field of Classification Search
CPC ....... A61K 33/00; A61K 9/0073; A61P 25/28; G01N 33/6863
See application file for complete search history.

(56) References Cited

U.S. PATENT DOCUMENTS

| 6,559,190 B1 | 5/2003 | Petzelt et al. |
| 2005/0255169 A1 | 11/2005 | Pilger et al. |

(Continued)

FOREIGN PATENT DOCUMENTS

| JP | 2009-051005 | 3/2009 |
| WO | 2005/034966 | 4/2005 |

(Continued)

OTHER PUBLICATIONS

Dobrovolsky et al., "Beneficial effects of xenon inhalation on behavioral changes in a valproic acid-induced model of autism in rats," Journal of Translational Medicine (2019) 17: 400 (pp. 1-15) (Year: 2019).*
Buonocore, G et al., "New Pharmacological Approaches in Infants with Hypoxic-Ischemic Encephalopathy", Current Pharmaceutical Design (2012), vol. 18, No. 21, pp. 3086-3100.

(Continued)

*Primary Examiner* — Aradhana Sasan
(74) *Attorney, Agent, or Firm* — Baumgartner Patent Law; Marc Baumgartner

(57) ABSTRACT

Described are compositions of matter and protocols useful for treatment of neurological and other disorders associated with inflammatory activities. In some embodiments the invention provides means of modulating neuroinflammation through administration of noble gas containing compositions. In other aspects, the invention provides means of modulating stem cell compartments to enhance endogenous reparative activities or to synergize with existing treatments.

4 Claims, 2 Drawing Sheets

(51) Int. Cl.
*A61P 25/28* (2006.01)
*G01N 33/68* (2006.01)

(56) References Cited

U.S. PATENT DOCUMENTS

| | | | |
|---|---|---|---|
| 2013/0302445 A1 | 11/2013 | Barbut et al. | |
| 2015/0359759 A1* | 12/2015 | Katz | A61K 45/06 514/229.5 |
| 2016/0151412 A1 | 6/2016 | Michel et al. | |

FOREIGN PATENT DOCUMENTS

| | | |
|---|---|---|
| WO | 2007/036900 | 4/2007 |
| WO | 2013/184202 | 12/2013 |
| WO | 2014/093277 | 6/2014 |
| WO | 2014/145443 | 9/2014 |
| WO | 2014/145485 | 9/2014 |
| WO | 2014/162010 | 10/2014 |
| WO | 2015/04371 | 1/2015 |

OTHER PUBLICATIONS

Fahlenkamp A V, et al., "The noble gas argon modifies extracellular signal-regulated kinase 1/2 signaling in neurons and glial cells", European Journal of Pharmacology, (2012), vol. 674, No. 2-3, pp. 104-111.

Pittet et al., "Systemic inflammatory response syndrome, sepsis, severe sepsis and septic shock: incidence, morbidities and outcomes in surgical ICU patients", Intensive Care Med. Apr. 1995;21(4):302-9.

Silverman et al., "Brain region-specific alterations in the gene expression of cytokines, immune cell markers and cholinergic system components during peripheral endotoxin-induced inflammation", Mol Med. Mar. 11, 2015;20:601-11. doi: 10.2119/molmed.2014.00147.

Ghanizadeh, A., "Hyperbaric oxygen therapy for treatment of children with autism: a systematic review of randomized trials", Med Gas Res. May 11, 2012;2:13. doi: 10.1186/2045-9912-2-13.

PCT International Search Report dated Oct. 27, 2016 in PCT/US2016/039038 (3 pages).

English translation of Office Action dated Sep. 18, 2018 issued in Japanese Patent Application No. 2017-567439.

* cited by examiner

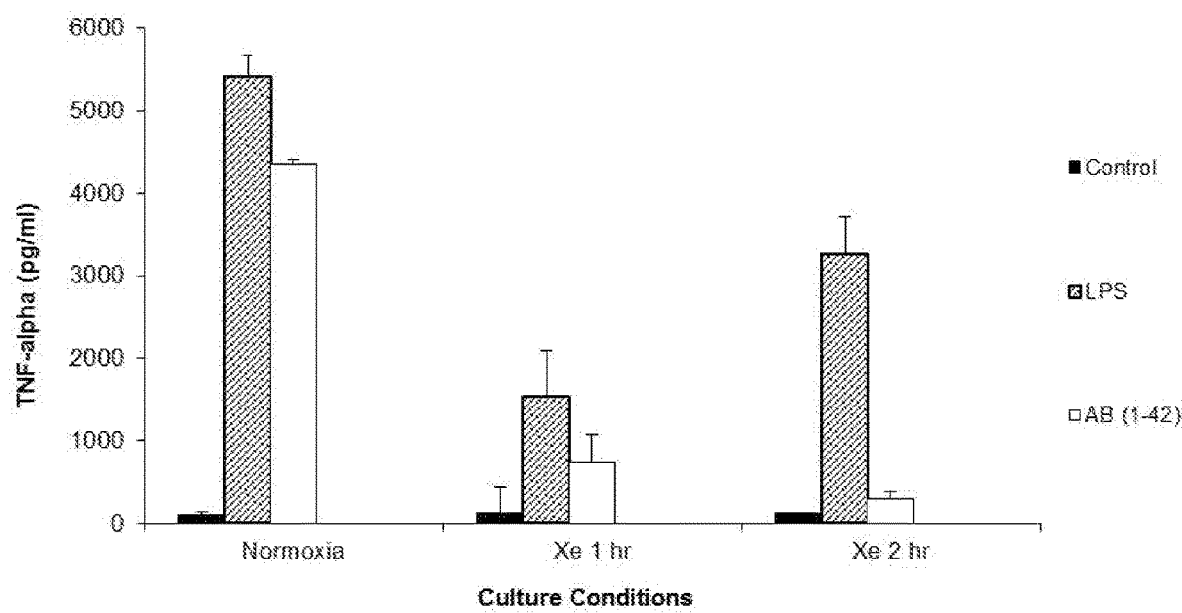
Figure 1: Suppression of Inducible TNF alpha Production from Monocytes by Xenon

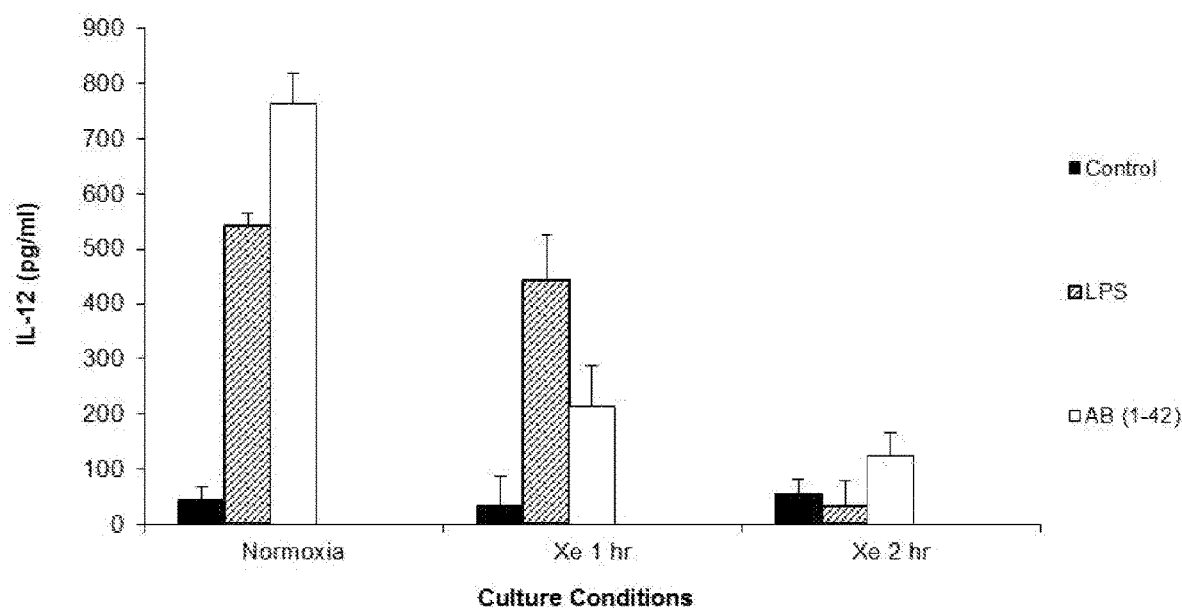
Figure 2: Suppression of Inducible IL-12 Production from Dendritic Cells by Xenon

THERAPEUTIC IMMUNE MODULATION USING NOBLE GAS COMPOSITIONS

CROSS REFERENCE TO RELATED APPLICATIONS

This application is a U.S. national phase of International Application No. PCT/US2016/039038, filed Jun. 23, 2016 and, claims the benefit of U.S. Provisional Application No. 62/183,624, filed Jun. 23, 2015, and to U.S. Provisional Application No. 62/276,753, filed Jan. 8, 2016, which are hereby expressly incorporated by reference in their entirety.

FIELD OF THE INVENTION

The invention relates to the field of autism spectrum disorders (ASD), more specifically, the invention relates to the use of various mixtures of noble gases to decrease inflammatory mediators associated with ASD.

BACKGROUND OF THE INVENTION

Autism spectrum disorders (ASD) are a group of diseases characterized by varying degrees of impairment in communication skills, social interactions, and restricted, repetitive and stereotyped patterns of behavior. The difference in the diseases depends on the time of onset, the rate of symptom development, the severity of symptoms, and the exact nature of the symptoms. These disorders range from mild to severe impairment and include such diseases as autism, Asperger's syndrome, PDD-NOS, Rett's disorder, childhood disintegrative disorder, semantic communication disorder, non-verbal learning disabilities, high functioning autism, hyperlexia and some aspects of attention deficit hyperactivity disorder.

While the exact number of children with autism spectrum disorders is unclear, rates in localized areas of the United States vary from 3.4 children per one thousand to 6.7 children per one thousand. Further, recent studies estimate that 15,000 children aged three through five years, and 78,000 children and young adults aged six through twenty-one years in the United States have autism. Rates in Europe and Asia are similar, with as many as six per one thousand children having at least one autism spectrum disorder. Additionally, there are number of related disorders including anxiety disorders, obsessive-compulsive disorders, social deficit disorders, repetitive disorders and cognitive deficit disorders which exhibit symptoms similar to those displayed in autism spectrum disorders, greatly increasing the size of the affected population.

ASDs are considered a class of severe heterogeneous neuro-developmental conditions characterized by inability to properly engage in social interactions and communication. Additionally, patients with this conditions suffer from lack of interest in their surroundings, accompanied by repetitive, and stereotypic verbal and non-verbal behaviors. Additional characteristics of autism spectrum disorders include social withdrawal and averted gaze including an inability to make eye contact, repetitive behaviors and obsessions, stereotyped movements, anxiety, attention deficit, hyperactivity, depression, a reclusive personality, and the inability to understand feelings. Patients afflicted with autism spectrum disorders may have an aversion to physical affection or contact, ignore communication from others, or if socially engaged, demonstrate a marked inability to communicate or relate to others. Communication difficulties may manifest as a monotone voice, an inability to control the volume of their voice, echolalia or an inability to talk at all. Individuals with autism spectrum disorders may also suffer from visual difficulties, comprehension difficulties, sound and light sensitivity and mental retardation. There have been a number of potential causes of autism, although little conclusive evidence for specific ones exists. ASD development is considered to be multifactorial and polygenic influences. Studies have made associations between autism and infectious agents, air pollution, organophosphates, heavy metals, maternal immune activation and vaccination. It is believed that the these factors are associated with induction of effector functions that manipulate normal neurodevelopmental processes through systemic and localized oxidative stress, endoplasmic reticulum stress, decreased methylation capacity, limited production of glutathione, mitochondrial dysfunction, intestinal dysbiosis, increased toxic metal burden, immune dysregulation, immune activation of neuroglial cells.

Numerous treatments have been attempted for treatment of ASD including; melatonin, acetylcholinesterase inhibitors, naltrexone, carnitine, stem cell thrapy, tetrahydrobiopterin, vitamin C, glutamate antagonists, special dietary supplements, hyperbaric oxygen treatment, immunomodulation and anti-inflammatory treatments, oxytocin, acupuncture, music therapy, and vision therapy. Medications prescribed by conventional physicians for autism address specific symptoms such as anxiety and depression and include agents such as fluoxetine, fluvoxamine, sertraline and clomipramine. Antipsychotic medications such as chlorpromazine, thioridazine, and haloperidol have been used to treat behavioral problems. Anticonvulsants such as arbamazepine, lamotrigine, topiramate, and valproic acid have been given to prevent seizures. Although improvements in some situations have been reported, these have not been consistently successful in order to cause wide-spread acceptance. Accordingly, it is the purpose of the current invention to provide means of treating autism through administration of a novel gas-based therapeutic mixture.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows suppression of inducible TNF-alpha production from monocytes by xenon gas.

FIG. 2 shows suppression of inducible IL-12 production from dendritic cells by xenon gas.

DETAILED DESCRIPTION OF THE INVENTION

The invention teaches the use of Noble gas containing mixtures to decrease inflammatory cytokines produced systemically, and locally in the central nervous system. In one aspect of the invention, disclosed is the reduction of interferon gamma, IL-12, and IL-17 subsequent to administration of a Noble gas containing composition. In one aspect, the invention provides the assessment of systemic levels of these cytokines as a means of quantifying the intensity and duration of Noble gas containing composition to be administered to one suffering from a condition associated with production of inflammatory cytokines. In one aspect, the invention teaches assessment of levels of inflammatory cytokines produced by peripheral blood mononuclear cells after ex vivo stimulation with a mitogen, as a means of guiding need for intervention using Noble gas containing compositions. In one particular embodiment assessment of inflammatory cytokine production, and subsequent modulation by administration of Noble gas containing composition is performed in conditions of autism, and autism spectrum disorder. In one embodiment, said inflammatory cytokines are selected from a group comprising of: ABCF1, BCL6, C3, C4A, CEBPB, CRP, ICEBERG, IL1R1, IL1RN, IL8RB, LTB4R, TOLLIP, IFNA2, IL10RA, IL10RB, IL13, IL13RA1, IL5RA, IL9, IL9R, CD40LG (TNFSF5), IFNA2, IL17C, IL1A, IL1B, IL1F10, IL1F5, IL1F6, IL1F7, IL1F8, IL1F9, IL22, IL5, IL-6, IL8, IL9, IL-18, IL-33, LTA, LTB, MIF, SCYE1, SPP1, TNF, CCL13 (mcp-4), CCR1, CCR2, CCR3, CCR4, CCR5, CCR6, CCR7, CCR8, CCR9, CX3CR1, IL8RA, XCR1 (CCXCR1), C5, CCL1 (I-309), CCL11 (eotaxin), HMGB1, interferon gamma, IL-2. IL-12, IL-17, IL33. CCL13 (mcp-4), CCL15 (MIP-1d), CCL16 (HCC-4), CCL17 (TARC), CCL18 (PARC), CCL19, CCL2 (mcp-1), CCL20 (MIP-3a), complement components C3, and C5, 2,3 alpha gal, CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, and IL8

Noble gas containing compositions are selected from the gases xenon, helium, argon, neon, and kypton, with a preferred embodiment being xenon. In one embodiment of the invention adition of nitrous oxide and/or a nitrous oxide donor is added to said Noble gas containing compositions. Of particular importance, Noble gas compositions are administered at concentrations below those needed to induce an anesthetic effect. In one embodiment of the invention, said Noble gas containing compositions are comprised of a mixture of inhalable gases wherein xenon or xenon donor is equal to or less than about 50%. In another embodiment, xenon comprises approximately 15-40% of said gaseous composition, with a preferable concentration of approximately 25% xenon diluted in other gases, preferably oxygen or air. In some embodiments, said Noble gas containing composition is administered through the use of a hyperbaric chamber, said pressure in said hyperbaric chamber being no more than 3 atm (0.3 MPa).

Xenon, acts as an NMDA receptor antagonist, as taught by N. Franks et al, How does xenon produce anaesthesia? Nature, 396, 324. (1998), has an acute analgesic effect, as recalled by D. Ma et al., Xenon exerts age-independent antinociception in Fischer rats, Anesthesiology. 100, 1313-8. (2004), and S. Petersen-Felix et al, Comparison of the analgesic potency of xenon and nitrous oxide in humans evaluated by experimental pain; Br J Anaesth. 81, 742-7 (1998). WO-A-02/22141 teaches the use of xenon as a cardiovascular protective agent, sedative, and analgesic. The current patent applies the use of xenon and combinations of noble gases for the treatment of ASD.

In one embodiment of the invention, combinations of noble gases are utilized for treatment of neurological indications including obsessive-compulsive syndrome, bulemia, anorexia, agoraphobia, and claustrophobia. In one embodiment of the invention, combination of noble gases are utilized for treatment of generalized anxiety, major depression, schizoaffective disorder, schizophrenia, PTSD, autism, panic disorder, aspergers syndrome, organic brain syndromes: alzheimer's, lewy body, Parkinson's Disease, migraine headaches, Huntington's Disease, and addictions.

The invention provides means of treating patients suffering from ASD. The selection of patients is based around observations that specific patients with ASD suffer from local and systemic immune dysregulation, resulting in enhanced proclivity to inflammatory mediator production and excitotoxicity.

In one embodiment of the invention, mixtures of noble gases such as argon and xenon are administered to patients suffering from ASD in a manner sufficient to correct immunological abnormalities.

Early studies found that patients with autism actually possessed a deficiency in ability of T cells to multiply after stimulation with mitogens. In one study, Stubbs et al examined 12 patients who suffered from ASD and 13 control patients. Across a variety of concentrations of the T cell mitogen phytohemagglutinin (PHA), the investigators found depressed proliferation in the peripheral blood mononuclear cells of patients suffering from ASD as compared to controls [1]. Expansion of this study by an independent group, which examined 31 ASD patients and added conconavalin A and pokeweed mitogen, revealed again a suppression of lymphocyte proliferation in autistic patients as compared to age-matched controls [2]. Specific lymphocyte types that have been reported to be non-specifically reduced in ASD include CD4 T cells [3], and NK cells [4]. Although counter-intuitive, suppressed lymphocyte proliferative activity to non-specific stimuli is actually associated with autoimmune conditions. This has been demonstrated in patients with autoimmunity [5-9], as well as in animal models [10-12].

Given the dependence of B cells and antibody production on T cells, studies have also demonstrated deficiencies in the humoral arm of the immune system in patients with ASD. Heuer et al Plasma was collected from children with autistic disorder (AU; n=116), developmentally delayed (DD) but not autistic (n=32), autism spectrum disorder but not full autism (n=27), and age-matched typically developing (TD) controls (n=96). Samples were assayed for systemic levels of immunoglobulin (IgG, IgM, IgA, and IgE) by enzyme-linked immunosorbent assay. Subjects with autism were evaluated using the Autism Diagnostic Observation Schedule and the Autism Diagnostic Interview-Revised, and all subjects were scored on the Aberrant Behavior Checklist (ABC) by the parents. Numerical scores for each of the ABC subscales as well as the total scores were then correlated with Ig levels. It was found that children with AU have a significantly reduced level of plasma IgG (5.39+/−0.29 mg/mL) compared to the TD (7.72+/−0.28 mg/mL; P<0.001) and DD children (8.23+/−0.49 mg/mL; P<0.001). Children with autism also had a reduced level of plasma IgM (0.670.06 mg/mL) compared to TD (0.79+/−0.05 mg/mL; P<0.05). Most importantly Ig levels were negatively correlated with ABC scores for all children (IgG: r=−0.334, P<0.0001; IgM: r=−0.167, P=0.0285) [13]. A subsequent study repeated the observations of reduced antibody levels, both IgG and IgM in autistic patients [14]. Accordingly, one explanation for the reduced T cell activity may be inappropriate interaction between antigen presenting cells and developing T cells. It has been previously demonstrated that antigen presenting cell defects exist in autoimmunity, and these correlated with improper generation of T cell receptors, which allow for breaking of self tolerance [15-17]. Macrophages are one type of immune cell that presents antigens to T cells, suggesting a constitutive inflammatory state in ASD are studies showing plasma levels of MIF-1, a macrophage modulating molecule in patients [18]. Defects in molecules needed for proper antigen presentation have been found in ASD. For example, Jyonouchi et al found reduced ability of the toll like receptors (TLRs) to stimulate production of interleukin 10 [19]. This cytokine is a fundamental signal generated by antigen presenting cells which acts on T cells [20-22], and plays a fundamental role in the generation and maintenance of T regulatory cells which keep the immune system from initiation of autoimmunity [23, 24]. Thus in one aspect of the current invention, the inventors disclose the use of noble gas combinations to increase activity of T regulatory cells so as to induce a rebalancing of the immune system in patients suffering from ASD.

Supporting an immunological association with autism are studies in which antibodies are found in ASD patients but not in healthy controls, antibodies reactive to neurologically relevant targets. Silva et al, analyzed autoantibody repertoires to brain tissue extract in the plasma of 171 autism children, their parents, and 54 controls, by quantitative immunoblotting. Multiparametric analysis revealed significant differences between patients and controls, and showed reactivity to an area of the blot that had the power to discriminate between these samples. The molecular weight of the target protein suggested that it might be an isoform of Myelin Basic Protein (MBP), the protein that lines axons and is target in multiple sclerosis [25]. In another study, Vojdani et al investigated reactivity of sera from 50 autism patients and 50 healthy controls to specific peptides from gliadin and the cerebellum. Gliadin is the antigen found in gluten that is linked to gluten intolerance, a feature of numerous patients with ASD. A significant percentage of autism patients showed elevations in antibodies against gliadin and cerebellar peptides simultaneously. The authors concluded that a subgroup of patients with autism produce antibodies against Purkinje cells and gliadin peptides, which may be responsible for some of the neurological symptoms in autism [26]. In another study, Cabanlit et al. studied plasma from 172 individuals (Autistic (AU)), n=63, median age: 43 months; (typically developing (TD)) controls, n=63, median age: 48 months; siblings, n=25, median age: 61 months; and (developmentally delayed (DD)) controls, n=21, median age: 38 months). The plasma was analyzed by Western blot for the presence of IgG antibodies against protein extracts from specific regions of the human adult brain including the hypothalamus and thalamus. The investigators reported the presence of an approximately 52 kDa MW band, in the plasma of subjects with AU detected with a significantly higher incidence when compared to plasma from TD controls (29% vs. 8%, P=0.0027 and 30% vs. 11%, P=0.01, in the thalamus and hypothalamus, respectively). Reactivity to three brain proteins (42-48 kDa MW), in particular in the hypothalamus, were observed with increased incidence in 37% of subjects with AU compared to 13% TD controls (P=0.004). Multiple brain-specific autoantibodies presented at significantly higher frequency in children with AU. While the potential role of these autoantibodies in AU is currently unknown, their presence suggests a loss of self-tolerance to one or more neural antigens during early childhood [27]. Accordingly, in one aspect of the invention, methods of treatment of ASD are provided through the administration of noble gases in order to reduce antibody production targeting neurological tissues. In one embodiment, the invention teaches the utilization of noble gases together with other agents that modulate production of antibodies, said means of modulating antibodies may be specific to antigens, as for example in the case of antigen-specific tolerance induction (eg nasal tolerance, oral tolerance, intravenous tolerance, tolerogenic vaccines), or may be antigen-nonspecific such as administration of chemotherapeutic agents, rituximab, or plasmapheresis.

In another embodiment of the invention, xenon gas containing mixtures, in a preferred embodiment of 25% xenon diluted in air or oxygen, are administered to reduce IL-12 production from dendritic cells in a patient suffering from immune conditions in which reduction of IL-12 is desirable. In one embodiment said 25% xenon diluted in oxygen is administered at a volume of 10 liters per administration, with 3 administrations performed per week.

The autoimmune aspect of ASD is represented not only by elevated antibodies but also systemic expression of inflammatory proteins or cytokines. Given the knowledge that various inflammatory agents are associated with excitotoxicity, and some of the characteristics of ASD resemble phenotypes induced by inflammatory stimuli, rationale exists to search for inflammatory and anti-inflammatory mediators systemically in patients with ASD. An early study by Singh et al demonstrated that patients with ASD possess significantly higher levels of IL-12 and interferon gamma in systemic circulation as compared to non-affected controls. This is highly interesting in that it is well-known that IL-12 produced by the antigen presenting arm of the immune response is associated with triggering of Th1 cells, which in turn are known to be inflammatory [28]. In another study serum concentrations of tumor necrosis factor-a (TNF-a), interleukin-1 (IL-1) and interleukin-6 (IL-6) were measured in 65 autistic, 8 attention deficit disorder, 2 children with Rett's syndrome and 2 children with Asperger syndrome. The results were compared to age, and sex matched control children. A significantly increased production of TNF-a, IL-1 and IL-6 from the sera of autistic, attention deficit disorder, Rett's syndrome and Asperger syndrome children [29]. Given that TNF-a, IL-1 and IL-6 are all proinflammatory signals generated by the antigen presenting arm of the immune system, particularly macrophages, the study supports indirectly the presence of an alteration in this arm of the immune system in ASD.

In another study a clinical investigation was performed of differential cytokine release in plasma samples obtained from 2 to 5 year-old children with ASD compared with age-matched typically developing (TD) children and children with developmental disabilities other than autism (DD). Ninety-seven participants with a confirmed diagnosis of ASD using standard assessments (DSM IV criteria and ADOS, ADI-R), 87 confirmed TD controls, and 39 confirmed DD controls. Plasma was isolated and cytokine production was assessed by multiplex Luminex™ analysis. Observations indicate significant increases in plasma levels of a number of cytokines, including IL-1β, IL-6, IL-8 and IL-12p40 in the ASD group compared with TD control. Moreover, when the ASD group was separated based on the onset of symptoms, it was noted that the increased cytokine levels were predominantly in children who had a regressive form of ASD. In addition, increasing cytokine levels were associated with more impaired communication and aberrant behaviors. This study was of particular importance because severity of ASD was correlated with inflammatory markers [30]. Other additional cytokines have been described in ASD, for example, Al-Ayadhi et al interrogated serum IL-17A levels in 45 children with ASD and 40 matched healthy controls. Children with ASD had significantly higher serum IL-17A levels than healthy controls, with increased serum levels of IL-17A found in 48.9% of the autism group. Patients with severe autism had significantly higher serum IL-17A levels than those with mild to moderate autism, and raised serum IL-17A levels were significantly more common in children with severe autism (67.9%) than in those with mild to moderate autism (17.6%), P=0.001 [31].

Elevation of IL-17 in ASD is particularly indicative of an autoimmune component to this condition due to the fundamental importance of this cytokine in breaking of self-tolerance [32-36]. This is exemplified by its presence in many of the animal models of autoimmunity, as well as in patients [37-40].

The inflammatory cytokine leptin has also been reported in ASD patients. For example, Blardi et al. studied young autistic patients and examined plasma leptin and adiponectin levels over a year period. Thirty-five patients, mean age at the basal time 14.1+/−5.4 years, were enrolled. Controls were 35 healthy subjects, sex and age matched. Blood samples were withdrawn in the morning at the baseline and 1 year after. In patients leptin concentrations significantly increased, while adiponectin did not significantly change. Leptin values in patients were significantly higher than those found in controls at each time; adiponectin values did not differ at each time between patients and controls. Since patients were not obese, the authors hypothesized that leptin might participate to clinical manifestations other than weight balance [41]. Another study confirmed this finding. Specifically, leptin plasma levels were assessed in 70 children diagnosed with autism (including 37 with regression) compared with 99 age-matched controls including 50 typically developing (TD) controls, 26 siblings without autism, and 23 children with developmental disabilities (DD). Children with autism had significantly higher plasma leptin levels compared with TD controls (p<0.006). When further sub-classified into regression or early onset autism, children with early onset autism had significantly higher plasma leptin levels compared with children with regressive autism (p<0.042), TD controls (p<0.0015), and DD controls (p<0.004).

More extensive cytokine analysis was performed by Suzuki et al who utilized the multiplex assay for cytokines and chemokines to examine plasma samples from male subjects with high-functioning ASD (n=28) and matched controls (n=28). Among a total of 48 analytes examined, the plasma concentrations of IL-1β, IL-1RA, IL-5, IL-8, IL-12 (p70), IL-13, IL-17 and GRO-α were significantly higher in subjects with ASD compared with the corresponding values of matched controls after correction for multiple comparisons [42]. Similar results were found in another independent study [43]. Correlations have been made between numerous of these inflammatory mediators, and also chemokines, with severity of ASD. In another study, Ashwood et al. determined whether there were differential profiles of chemokines in the plasma of children with ASD compared to age-matched typically developing controls and children with developmental disabilities other than ASD. Increased MCP-1, RANTES and eotaxin levels were observed in ASD children compared with both control groups (p<0.03), and increased chemokine production was associated with higher aberrant behavior scores and more impaired developmental and adaptive function [44].

The association of inflammatory mediators with autism can be perhaps explained by increased levels of the proinflammatory molecule HMGB1 in plasma of ASD patients. For example, a study of 22 adult patients with autistic disorder (mean age: 28.1+/−7.7 years) and 28 age- and gender-matched healthy controls (mean age: 28.7+/−8.1 years) assessed levels of HMGB1 were measured by enzyme-linked immunosorbent assay (ELISA). Compared with healthy subjects, serum levels of HMGB1 were significantly higher in patients with autistic disorder (10.8+/−2.6 ng/mL versus 5.6+/−2.5 ng/mL, respectively, P<0.001). After adjustment for potential confounders, serum HMGB1 levels were independently associated with their domain A scores in the Autism Diagnostic Interview-Revised, which reflects their impairments in social interaction [45]. An alternative hypothesis, although not mutually exclusive, is that reduced levels of immune suppressive cytokines are found in patients with ASD. For example, TGF-beta is known to be a potent suppressor of inflammation and Th1/Th17 cytokines. Plasma levels of active TGF beta 1 were evaluated in 75 children with ASD compared with 68 controls. Children with ASD had significantly lower plasma TGF beta 1 levels compared with typically developing controls (p=0.0017) and compared with children with developmental disabilities other than ASD (p=0.0037), after adjusting for age and gender. In addition, there were significant correlations between psychological measures and TGF beta 1 levels, such that lower TGF beta 1 levels were associated with lower adaptive behaviors and worse behavioral symptoms [46].

Evidence of the biological relevance of cytokine dysregulation in ASD is that fact that systemic markers of inflammation are elevated. For example, neopterin, a product manufactured by activated macrophages is expressed at higher levels in ASD patients as compared to controls [47-49]. Additionally, nitric oxide, another marker of macrophage activation is also elevated in ASD patients [50].

In addition to cytokine abnormalities, cellular abnormalities have been detected, including alterations of ability of immune cells to produce cytokines in vitro upon stimulation. One study examined isolated peripheral blood monocytes from 17 children with ASD and 16 age-matched typically developing (TD) controls and stimulated these cell cultures in vitro with distinct toll-like receptors (TLR) ligands and supernatants were harvested from the cell cultures and pro-inflammatory cytokine responses for IL-1beta, IL-6, IL-8, TNFalpha, MCP-1, and GM-CSF were determined by multiplex Luminex analysis. After in vitro challenge with TLR ligands, differential cytokine responses were observed in monocyte cultures from children with ASD compared with TD control children. In particular, there was a marked increase in pro-inflammatory IL-1beta, IL-6, and TNFalpha responses following TLR 2, and IL-1beta response following TLR 4 stimulation in monocyte cultures from children with ASD as compared to TD controls [51].

At the level of T cells a clinical study investigated 66 children with a confirmed diagnosis of ASD and 73 confirmed typically developing (TD) controls 2-5 years-of-age. In vitro stimulation of peripheral blood mononuclear cells with PHA and tetanus was used to compare group-associated cellular responses. The production of GM-CSF, TNFα, and IL-13 were significantly increased whereas IL-12p40 was decreased following PHA stimulation in ASD relative to TD controls. Induced cytokine production was associated with altered behaviors in ASD children such that increased pro-inflammatory or T(H)1 cytokines were associated with greater impairments in core features of ASD as well as aberrant behaviors. In contrast, production of GM-CSF and T(H)2 cytokines were associated with better cognitive and adaptive function. Following stimulation, the frequency of CD3(+), CD4(+) and CD8(+) T cells expressing activation markers CD134 and CD25 but not CD69, HLA-DR or CD137 were significantly reduced in ASD, and suggests an altered activation profile for T cells in ASD [52]. This has also been reviewed in the following references [53, 54].

The possibility that ASD is an immunologically mediated condition is supported by studies in which immune modulators inhibit ASD or reduce symptoms. For example, pioglitazone, an approved PPAR-gamma inhibitor which possesses anti-inflammatory properties was administered at either 30 or 60 mg per day p.o. A total of 25 children (average age 7.9+/−0.7 year old) were enrolled. Behavioral symptoms were assessed by the Aberrant Behavior Checklist (ABC), which measures hyperactivity, inappropriate speech, irritability, lethargy, and stereotypy, done at baseline and after 3-4 months of treatment. It was reported that daily treatment with 30 or 60 mg p.o. pioglitazone for 3-4 months induced apparent clinical improvement without adverse events. There were no adverse effects noted and behavioral measurements revealed a significant decrease in 4 out of 5 subcategories (irritability, lethargy, stereotypy, and hyperactivity) [55]. The anti-inflammatory, NF-kB inhibitory drug pentoxyfilline was assessed in combination with respirodone in 40 children between the ages 4 and 12 years with a DSM IV-TR clinical diagnosis of ASD. The children presented with a chief complaint of severely disruptive symptoms related to autistic disorder. Patients were randomly allocated to pentoxifylline+risperidone or placebo+risperidone for a 10-week, double-blind, placebo-controlled study. The dose of risperidone was titrated up to 3 mg/day, pentoxifylline was titrated to 600 mg/day. Patients were assessed at baseline and after 2, 4, 6, 8 and 10 weeks of starting medication. The measure of the outcome was the Aberrant Behavior Checklist-Community (ABC-C). The difference between the two protocols was significant as the group that received pentoxyfylline had greater reduction in ABC-C subscale scores for Irritability, Lethargy/Social Withdrawal, Stereotypic Behavior, Hyperactivity/Noncompliance and Inappropriate Speech [56]. Other immune modulators associated with inhibition of inflammation such as IVIG [57], and steroids [58], have demonstrated some level of improvement.

One additional area of investigation supporting the hypothesis of ASD being an inflammatory/autoimmune condition derives from genetic studies in which association of genetic polymorphisms with immune associated genes such as HLA are associated with disease [59-69].

Overall, numerous evidences support the neuroimmune basis of ASD, these are reviewed in more detail in the following references [70-76].

Posttraumatic stress disorder (PTSD) is a debilitating trauma-related disorder resulting from exposure to a terrifying event or events. Although the majority of PTSD cases are associated with combat situations [77], other inciting factors have been reported [78-82]. Most biological findings in PTSD are compatible with those of the chronic stress response, such as increased corticotropin-releasing factor (CRF) concentrations and catecholamine depletion within the central nervous system [83]. Patients exhibit a broad range of problems with memory, including gaps in memory, problems with declarative memory, attentional biases to trauma-related information, and intrusive memories [84].

Anatomic differences have been found in patients with PTSD, for example, Bremner et al examined hippocampal volume in 26 Vietnam combat veterans with PTSD and 22 comparison subjects selected to be similar to the patients in age, sex, race, years of education, socioeconomic status, body size, and years of alcohol abuse. They observed that PTSD patients had a statistically significant 8% smaller right hippocampal volume relative to that of the comparison subjects, but there was no difference in the volume of other brain regions (caudate and temporal lobe) [85]. Other studies have found similar results in terms of decreased hippocampal volumes [86, 87].

Treatments for PTSD include the antidepressant paroxetine (Paxil) which is the most potent inhibitor of the reuptake of serotonin of all selective serotonin reuptake inhibitors (SSRIs) [88]. Marshall et al performed a double blind trial in which 186 patients were randomized to receive placebo, 183 to receive 20 mg/day of paroxetine, and 182 patients received 40 mg/day. Paroxetine-treated patients in both dose groups demonstrated significantly greater improvement on primary outcome measures compared to placebo-treated patients in the intent-to-treat analysis. Moreover, paroxetine treatment resulted in statistically significant improvement compared to placebo on all three PTSD symptom clusters (reexperiencing, avoidance/numbing, and hyperarousal), social and occupational impairment, and comorbid depression. Treatment response did not vary by trauma type, time since trauma, or severity of baseline PTSD or depressive symptoms. Both doses were well tolerated [89]. These results were reproduced by several other studies [90-93].

PTSD is characterized by neuroinflammation [94-96], as well as systemic upregulation of inflammatory markers [97, 98]. Interestingly agents that reduce inflammation such as minocycline also possess activity against PTSD or models of PTSD [99, 100]. Principles utilized to reduce neuroinflammation and inflammation, and to modify biological processes associated with PTSD and autism are also applicable to other psychiatric and neurological conditions including stroke, schizophrenia, and dementia. In one embodiment of the invention, noble gas containing mixtures are utilized for reduction of inflammation in patients with PTSD. In one embodiment of the invention, stimulation of neurogenesis is accomplished by administration of noble gas containing mixtures. In one embodiment, use of noble gas containing mixtures for treatment of stroke, schizophrenia, and dementia is disclosed. In one embodiment said noble gas containing mixture is comprised of a concentration of xenon of approximately 10-40% by volume. In another embodiment, said concentration of xenon is approximately 15-25% by volume. Remaining concentration of gas may be air, mixtures of oxygen and nitrogen, or addition of other noble gases.

Guidance for determination of concentrations and ratios of noble gas containing mixtures are provided in the art, which are used based on the desired effect. Examples of noble gas containing mixtures useful for elicitation of neurological/immunological effects are given in the following papers which are incorporated by reference [101-106]. In one embodiment, said mixture of noble gases are capable of physiological administration as a the gaseous composition to the patient by inhalation wherein the gaseous composition contains an effective volume proportion of xenon, lying between at least 10% and less than 50% by volume, and sufficient to modulate immunological parameters in a patient in need of therapy. In another embodiment, the gaseous mixture is administered to induce neurogenesis. In another embodiment said gaseous mixture is administered to reduce excitotoxicity. In another embodiment said gaseous mixture is administered to treat a neurological condition. In one embodiment, said gaseous composition contains less than 40% by volume of xenon. In one embodiment the gaseous composition contains less than 30% by volume of xenon. In one embodiment said gaseous composition further contains oxygen. In one embodiment, said gaseous composition contains 21% by volume of oxygen. In one embodiment said gaseous composition further contains an additional compound selected from the group constituted by $N_2O$, Ar, Kr, Ne, He, Ne, NO, CO, $H_2S$ and $N_2$. In one embodiment, said gaseous composition is administered to the patient one or more times per day during an inhalation period of a few minutes to one or more hours. In one embodiment said gaseous composition is provided in a gas bottle at a pressure lying between 2 and 300 bar. Depending on the individual case, the inhalable gaseous composition according to the invention can include one or more of the following characteristics: it contains an effective volume proportion of xenon. It contains between 5 and 70% by volume of xenon. It contains at least 10% by volume of xenon. It contains less than 50% by volume of xenon. It contains less than 40% by volume of xenon, preferably less than 30% by volume of xenon. It further contains oxygen, preferably at least 21% by volume of oxygen. It further contains an additional compound selected from the group constituted by $N_2O$, Ar, Kr, He, Ne, NO, CO, $H_2S$ and $N_2$. The xenon is administered to the patient by inhalation one or more times per day, during a total treatment period of several days to several years. The gaseous xenon is mixed with a gas containing oxygen, in particular the xenon is mixed with air or an $N_2/O_2$ mixture.

In one embodiment of the invention, PTSD associated inflammation is treated by administration of 25% xenon, diluted either in air, or oxygen, at a volume of approximately 10 liters, said gas combination administered approximately 3 times per week. Examples of gases or gas mixtures employed as medicament for reduction of inflammation in conditions associated with inflammation of the central nervous system, such as PTSD, include: 1.) 100% by volume xenon; 2.) 70% by volume xenon/30% by volume oxygen; 3.) 65% by volume xenon/30% by volume oxygen/5% by volume nitrogen; 4.) 65% by volume xenon/35% by volume oxygen; 5.) 60% by volume xenon/30% by volume oxygen/10% by volume nitrogen; 6.) 60% by volume xenon/35% by volume oxygen/5% by volume nitrogen; 7.) 60% by volume xenon/40% by volume oxygen; 8.) 55% by volume xenon/25% by volume oxygen/20% by volume nitrogen; 9.) 55% by volume xenon/30% by volume oxygen/15% by volume nitrogen; 10.) 55% by volume xenon/35% by volume oxygen/10% by volume nitrogen; 11.) 55% by volume xenon/40% by volume oxygen/5% by volume nitrogen; 12.) 55% by volume xenon/45% by volume oxygen; 13.) 50% by volume xenon/50% by volume oxygen; 14.) 50% by volume xenon/45% by volume oxygen/5% by volume nitrogen; 15.) 50% by volume xenon/40% by volume oxygen/10% by volume nitrogen; 16.) 50% by volume xenon/30% by volume oxygen/20% by volume nitrogen; 17.) 50% by volume xenon/25% by volume oxygen/25% by volume nitrogen; 18.) 45% by volume xenon/55% by volume oxygen; 19.) 45% by volume xenon/50% by volume oxygen/5% by volume nitrogen; 20.) 45% by volume xenon/45% by volume oxygen/10% by volume nitrogen; 21.) 45% by volume xenon/40% by volume oxygen/15% by volume nitrogen; 22.) 45% by volume xenon/35% by volume oxygen/20% by volume nitrogen; 23.) 45% by volume xenon/30% by volume oxygen/25% by volume nitrogen; 24.) 45% by volume xenon/30% by volume oxygen/25% by volume nitrogen; 25.) 40% by volume xenon/30% by volume oxygen/30% by volume nitrogen; 26.) 40% by volume xenon/50% by volume oxygen/10% by volume nitrogen; 27.) 35% by volume xenon/25% by volume oxygen/40% by volume nitrogen; 28.) 35% by volume xenon/65% by volume oxygen; 29.) 30% by volume xenon/70% by volume oxygen; 30.) 30% by volume xenon/50% by volume oxygen/20% by volume nitrogen; 31.) 30% by volume xenon/30% by volume oxygen/40% by volume nitrogen; 32.) 20% by volume xenon/80% by volume oxygen; 33.) 20% by volume xenon/30% by volume oxygen/50% by volume nitrogen; 34.) 15% by volume xenon/30% by volume oxygen/55% by volume nitrogen; 35.) 15% by volume xenon/50% by volume oxygen/35% by volume nitrogen; 36.) 10% by volume xenon/90% by volume oxygen; 37.) 10% by volume xenon/50% by volume oxygen/40% by volume nitrogen; 38.) 10% by volume xenon/30% by volume oxygen/60% by volume nitrogen; 39.) 10% by volume xenon/25% by volume oxygen/65% by volume nitrogen; 40.) 5% by volume xenon/25% by volume oxygen/70% by volume nitrogen; 41.) 5% by volume xenon/30% by volume oxygen/65% by volume nitrogen; 42.) 5% by volume xenon/50% by volume oxygen/45% by volume nitrogen; 43.) 5% by volume xenon/30% by volume oxygen/65% by volume nitrogen; 44.) 5% by volume xenon/95% by volume oxygen; 45.) 1% by volume xenon/99% by volume oxygen; 46.) 1% by volume xenon/30% by volume oxygen/69% by volume nitrogen; 47.) 1% by volume xenon/25% by volume oxygen/74% by volume nitrogen.

in one embodiment of the invention, therapeutic Noble Gas compositions are administered in a manner to alter immunological factors in the body. Specifically, the invention teaches that various concentrations of xenon gas, when delivered into circulation, either by inhalation [107-109], or administration of echogenic xenon liposomes [110, 111], can be utilized to induce a T regulatory cell phenotype and suppression of Th17 or other arthritogenic cells. The use of xenon has been reviewed by numerous authors in the art, which provide guidance as to details of administration [112-114]. Importantly, the new and non-obvious aspect of the current invention is that xenon, as well as other Noble gases, are capable of inducing immune modulation to inhibit inflammation in the central nervous system.

In one embodiment of the invention, a regenerative cell population such as mesenchymal stem cells are initially "primed" with a noble gas containing mixture. Said "priming" is performed in order to enhance regenerative cell activity. Activities of interest for therapeutic purposes include enhancement of migration, enhancement of cytokine production, or enhancement of antiapoptotic activity. Concentrations and mixtures useful for obtaining such therapeutic activities are determined by stimulation of genes of interest, said genes related to said therapeutic activities. For example, when enhanced stem cell migration is desired, assessment for production of CXCR4 is performed. Means of performing this are well known in the art and include flow cytometic assessment of CXCR4. Other means of quantifying desired outcomes in terms of migration include SDF-1 migration assay. For assessment of regenerative activities after Noble gas containing compositions are administered, one of skill in the art may examine cytokines known to alter inflammatory or regenerative processes. Cytokines of relevance for the practice of the current invention include BLC, Eotaxin-1, Eotaxin-2, G-CSF, GM-CSF, I-309, ICAM-1, IL-1 ra, IL-2, IL-4, IL-5, IL-6 sR, IL-7, IL-10, IL-13, IL-16, MCP-1, M-CSF, MIG, MIP-1 alpha, MIP-1 beta, MIP-1 delta, PDGF-BB, RANTES, TIMP-1, TIMP-2, TNF alpha, TNF beta, sTNFRI, sTNFRIIAR, BDNF, bFGF, BMP-4, BMP-5, BMP-7, b-NGF, EGF, EGFR, EG-VEGF, FGF-4, FGF-7, GDF-15, GDNF, Growth Hormone, HB-EGF, HGF, IGFBP-1, IGFBP-2, IGFBP-3, IGFBP-4, IGFBP-6, IGF-1, Insulin, M-CSF R, NGF R, NT-3, NT-4, Osteoprotegerin, PDGF-AA, PlGF, SCF, SCF R, TGFalpha, TGF beta 1, TGF beta 3, VEGF, VEGFR2, VEGFR3, VEGF-D 6Ckine, Ax1, BTC, CCL28, CTACK, CXCL16, ENA-78, Eotaxin-3, GCP-2, GRO, HCC-1, HCC-4, IL-9, IL-17F, IL-18 BPa, IL-28A, IL-29, IL-31, IP-10, I-TAC, LIF, Light, Lymphotactin, MCP-2, MCP-3, MCP-4, MDC, MIF, MIP-3 alpha, MIP-3 beta, MPIF-1, MSPalpha, NAP-2, Osteopontin, PARC, PF4, SDF-1 alpha, TARC, TECK, TSLP 4-1BB, ALCAM, B7-1, BCMA, CD14, CD30, CD40 Ligand, CEACAM-1, DR6, Dtk, Endoglin, ErbB3, E-Selectin, Fas, Flt-3L, GITR, HVEM, ICAM-3, IL-1 R4, IL-1 RI, IL-10 Rbeta, IL-17R, IL-2Rgamma, IL-21R, LIMPII, Lipocalin-2, L-Selectin, LYVE-1, MICA, MICB, NRG1-beta1, PDGF Rbeta, PECAM-1, RAGE, TIM-1, TRAIL R3, Trappin-2, uPAR, VCAM-1, XEDARActivin A, AgRP, Angiogenin, Angiopoietin 1, Catheprin S, CD40, Cripto-1, DAN, DKK-1, E-Cadherin, EpCAM, Fas Ligand, Fcg RIIB/C, Follistatin, Galectin-7, ICAM-2, IL-13 R1, IL-13R2, IL-17B, IL-2 Ra, IL-2 Rb, IL-23, LAP, NrCAM, PAI-1, PDGF-AB, Resistin, SDF-1 beta, sgp130, ShhN, Siglec-5, ST2, TGF beta 2, Tie-2, TPO, TRAIL R4, TREM-1, VEGF-C, VEGFR1Adiponectin, Adipsin, AFP, ANGPTL4, B2M, BCAM, CA125, CA15-3, CEA, CRP, ErbB2, Follistatin, FSH, GRO alpha, beta HCG, IGF-1 sR, IL-1 sRII, IL-3, IL-18 Rb, IL-21, Leptin, MMP-1, MMP-2, MMP-3, MMP-8, MMP-9, MMP-10, MMP-13, NCAM-1, Nidogen-1, NSE, OSM, Procalcitonin, Prolactin, PSA, Siglec-9, TACE, Thyroglobulin, TIMP-4, TSH2B4, ADAM-9, Angiopoietin 2, APRIL, BMP-2, BMP-9, C5a, Cathepsin L, CD200, CD97, Chemerin, DcR3, FABP2, FAP, FGF-19, Galectin-3, HGF R, IFN-gammalpha/beta ?R2, IGF-2, IGF-2 R, IL-17BR, IL-24, IL-33, Kallikrein 14, Legumain, LOX-1, MBL, Neprilysin, Notch-1, NOV, Osteoactivin, PD-1, PGRP-5, Serpin A4, sFRP-3, Thrombomodulin, TLR2, TRAIL R1, Transferrin, WIF-1ACE-2, Albumin, AMICA, Angiopoietin 4, BAFF, CA19-9, CD163, Clusterin, CRTAM, CXCL14, Cystatin C, Decorin, Dkk-3, DLL1, Fetuin A, aFGF, FOLR1, Furin, GASP-1, GASP-2, GCSF R, HAI-2, IL-17B R, IL-27, LAG-3, LDL R, Pepsinogen I, RBP4, SOST, Syndecan-1, TACI, TFPI, TSP-1, TRAIL R2, TRANCE, Troponin I, uPA, VE-Cadherin, WISP-1, and RANK.

Various populations of mesenchymal stem cells may be used for the practice of the invention, in addition to bone marrow, adipose, or umbilical cord derived mesenchymal stem cells, amniotic membrane mesenchymal stem cells may be utilized as immune modulatory cells. In one specific embodiment, 8_8 cm2 sections of amniotic membrane are obtained. They were washed with 1.0M phosphate-buffered saline (PBS; pH 7.2) containing 300 IU/ml penicillin and 300 mg/ml streptomycin (Gibco, Grand Island, N.Y., USA), and are immediately immersed in Dulbecco's modified Eagle's medium (DMEM)-high glucose (Gibco), supplemented with 10% fetal bovine serum (FBS; Gibco), 300 IU/ml penicillin and 300 mg/ml streptomycin. All samples are processed within 12-15 h after collection. The amniotic membranes are treated with 0.1% collagenase I (Sigma-Aldrich, St Louis, Mo., USA) in 1.0M PBS (pH 7.2) and are incubated at 37_C for 20 min. Each amniotic membrane is washed three times with low-glucose DMEM (Gibco), and the detached cells are harvested after a gentle massage of the amniotic membrane. The cells are centrifuged at 300 g for 10 min at 37_C, and subsequently resuspended in RPMI 1640 medium with 10% FBS, then grown in 25 cm2 flasks at a density of 1_106 cells/ml. After 24 h incubation, nonadherent cells are removed. The culture medium is replaced every 3 days. Adherent cells are cultured until they reached 80-90% confluence. Cells are subsequently selected based on quality control procedures including purity (eg >90% CD90 and CD105 positive), sterility (eg lack of endotoxin and mycoplasma/bacterial contamination) and potency (eg ability to immune modulate in vitro by suppressing production of inflammatory cytokines such as IFN-gamma). Cells may subsequently be utilized for perilymphatic or intralymphatic administration. Without departing from the spirit of the invention, mesenchymal stem cells may be optimized to possess heightened immune modulatory properties. In one embodiment this may be performed by exposure of mesenchymal stem cells to hypoxic conditions, specifically hypoxic conditions can comprise an oxygen level of lower than 10%. In some embodiments, hypoxic conditions comprise up to about 7% oxygen. For example, hypoxic conditions can comprise up to about 7%, up to about 6%, up to about 5%, up to about 4%, up to about 3%, up to about 2%, or up to about 1% oxygen. As another example, hypoxic conditions can comprise up to 7%, up to 6%, up to 5%, up to 4%, up to 3%, up to 2%, or up to 1% oxygen. In some embodiments, hypoxic conditions comprise about 1% oxygen up to about 7% oxygen. For example, hypoxic conditions can comprise about 1% oxygen up to about 7% oxygen; about 2% oxygen up to about 7% oxygen; about 3% oxygen up to about 7% oxygen; about 4% oxygen up to about 7% oxygen; about 5% oxygen up to about 7% oxygen; or about 6% oxygen up to about 7% oxygen. As another example, hypoxic conditions can comprise 1% oxygen up to 7% oxygen; 2% oxygen up to 7% oxygen; 3% oxygen up to 7% oxygen; 4% oxygen up to 7% oxygen; 5% oxygen up to 7% oxygen; or 6% oxygen up to 7% oxygen. As another example, hypoxic conditions can comprise about 1% oxygen up to about 7% oxygen; about 1% oxygen up to about 6% oxygen; about 1% oxygen up to about 5% oxygen; about 1% oxygen up to about 4% oxygen; about 1% oxygen up to about 3% oxygen; or about 1% oxygen up to about 2% oxygen. As another example, hypoxic conditions can comprise 1% oxygen up to 7% oxygen; 1% oxygen up to 6% oxygen; 1% oxygen up to 5% oxygen; 1% oxygen up to 4% oxygen; 1% oxygen up to 3% oxygen; or 1% oxygen up to 2% oxygen. As another example, hypoxic conditions can comprise about 1% oxygen up to about 7% oxygen; about 2% oxygen up to about 6% oxygen; or about 3% oxygen up to about 5% oxygen. As another example, hypoxic conditions can comprise 1% oxygen up to 7% oxygen; 2% oxygen up to 6% oxygen; or 3% oxygen up to 5% oxygen. In some embodiments, hypoxic conditions can comprise no more than about 2% oxygen. For example, hypoxic conditions can comprise no more than 2% oxygen.

In the area of psychiatric disorders, areas for the utilization of compositions containing Noble gases include bipolar disorder, panic attacks, generalized anxiety, dementia, organic brain syndrome, cerebral palsy, coma, persistent vegetative state, minimally conscious state, global cerebral ischemia, traumatic brain injury, stroke, and post stroke recovery. The invention may be utilized for treatment of deficiencies of red blood cell production or for other hematopoietic deficiencies. Example include anemias, aplastic anemia, or myelodysplastic syndrome. In the particular example of aplastic anemia, concentrations of xenon, xenon/argon, xenon/argon/nitrogen are administered in order to enhance hematopoiesis, while suppressing TNF-alpha production.

EXAMPLES

Example 1

Combination of Xenon/Oxygen, Argon/Oxygen and Xenon/Argon/Oxygen Inhalations for Treatment of Childhood Autism Autism is a severe neurodevelopmental disorder that affects up to 16 in 10,000 individuals. It is a pervasive developmental disorder affecting social, communicative, and compulsive/repetitive behaviors characterized by stereotypic complex hand and body movements, craving for sameness, and narrow repetitive interests. Autism severely impacts both the affected individual and family members.

The proposed study is designed to assess the efficacy of treatment with Xenon/Oxygen, Argon/Oxygen and Xenon/Argon/Oxygen inhalations (later: Xenon/Argon/Oxygen inhalations vs. Placebo in childhood/adolescent autism fulfilling DSM-IV and Autism Diagnostic Interview (ADI) criteria.

Condition Intervention Phase
Autism
Childhood Autism
Drug: Xenon/Argon/Oxygen inhalations
  Phase 1
Study Type: Interventional
Study Design: Allocation: Randomized
Endpoint Classification: Safety/Efficacy Study
Intervention Model: Single Group Assignment
Masking: Double-Blind
Primary Purpose: Treatment
Official Title: Xenon/Argon/Oxygen inhalations Versus Placebo in Childhood Autism
  Primary Outcome Measures:
Autism Diagnostic Observation Schedule-Generic (ADOS-G)—Change from Baseline to Final Visit
Clinical Global Impression Improvement (CGI)—Change from Baseline to Final Visit
Aberrant Behavior Checklist (ABC) (hyperactivity/irritability sections)—Change from Baseline to Final Visit
Vineland Adaptive Behavior Scale—Change from Baseline to Final Visit
MacArthur Communicative Development Inventory (MCDI)—Change from Baseline to Final Visit
Conners' Parent Rating Scale-Revised: Long form (CPRS-R:L)—Change from Baseline to Final Visit
  Estimated Enrollment: 40
  Detailed Description:
Once enrolled in the study, subjects will receive evaluations and testing to determine if they meet the necessary criteria for admission into study treatment. Subjects will not be responsible for the costs of any evaluations or tests conducted as part of this study.

First, subjects will receive a psychiatric and medical evaluation by the study psychiatrist to see if she/he has any psychiatric or medical illnesses that would interfere with their ability to participate in this study. These evaluations may take up to an hour to complete. In addition, subjects will be asked to participate in a psychiatric interview designed to determine the child's diagnosis and current problem areas. The subject's parent will also be asked to fill out psychiatric questionnaires. The interview and questionnaires may take up to 4 hours to complete.

Second, urine and blood samples will be needed for routine tests two times during this study (before any study related tests are done, and at the end of the study). Two teaspoons of blood will be drawn each time. The urine sample will be analyzed in order to assess kidney function and to screen for the presence of drugs (such as cocaine, marijuana, heroin, etc.). A positive drug screen would result in the inability of the child to participate in this study. Drug screen results will be kept confidential. In addition, an electrocardiogram will be performed to determine heartbeat.

Lastly, a pregnancy test will be conducted on the urine sample if the child is female and has reached puberty. The child should not be in this study if she is pregnant or a nursing mother. A positive urine pregnancy test would cause the child to be removed from the study. If the child is sexually active, she must be using an effective method of birth control during her participation in this study. Acceptable methods of birth control are oral contraceptive medications (the administration of which must be parentally supervised), IUD, depot medication and tubal ligation.

Subjects will be assigned by chance to receive either the active medication Xenon/Argon/Oxygen inhalations or placebo (Room Air) for 12 weeks, much like the flip of a coin. Neither the parent/child nor the investigator will know which of the two treatments the child is receiving. The child has a 25% chance of being assigned to receive placebo during the study or the active medication, Xenon/Argon/Oxygen inhalations, during the study.

The child will need to be seen weekly by the study psychiatrist for the first 4 weeks of the twelve-week study, and every other week for the remaining weeks of the study. During these visits the study psychiatrist will ask the parent for feedback on his/her child's condition and any changes that may be related to the medication, including possible side effects, such as nausea and headaches, and will check the child's condition. The psychiatrist will also record his/her weight. These study visits will generally last approximately 30 minutes.

Eligibility
Ages Eligible for Study: 5 Years to 17 Years
Genders Eligible for Study: Both
Accepts Healthy Volunteers: No
  Criteria
Meets DSM-IV, ADI-R and ADOS-G criteria for autistic disorder
Age 5-17 years
Outpatients
Parent or legal guardian willing to sign informed consent.
Male or female patients
  Patient scores at least a "4" (moderately ill) on the Clinical Global Impression Scale for Autistic Disorder (CGI AD).
  Children who are minimally or non-verbal as indicated by a score of 50% of an 18 month old on the MacArthur Communicative Development Inventory
  Exclusion Criteria:
  Subjects with any of the following past or present mental disorders: psychotic disorders, mood disorders, including bipolar disorders.
  Subjects who have displayed significant self-injurious behavior (children who have caused visible harm to themselves).
  Subjects with active seizure disorder (seizures within the past six months).
  Subjects with clinically significant or unstable medical illness, including patients with current evidence of clinically significant hematopoietic, or cardiovascular disease.
  Subjects with present or history of the following:
  gastrointestinal, liver, kidney, or other known conditions which will presently interfere with the absorption, distribution, metabolism, or excretion of drugs,
  seizure disorders (active), cerebrovascular disease or brain trauma as etiology of autistic behavior,
  clinically significant unstable endocrine disorder, such as hypo- or hyperthyroidism or diabetes,
  recent history or presence of any form of malignancy.
  Subjects who report significant improvement of autism symptoms and behaviors to current medications or have only global autism ratings on the CGI of absent, minimal or mild severity, or who are more than minimally verbal.

Subjects whose global autism ratings are assessed as being absent, minimal or mild.

Treatment within the previous 30 days with any drug known to have a well-defined potential for toxicity to a major organ.

Subjects with clinically significant abnormalities in laboratory tests or physical exam.

Subjects likely to require any other psychotropic medication during the study, with the exception of clonidine for insomnia (started at least one month prior to entrance into the study), as well as anticonvulsants at a constant dose for stable seizure disorder or, unless otherwise permitted.

Subjects unable to tolerate taper from psychoactive medication, if specified.

Subjects with a history of hypersensitivity or severe side effects associated with the use of Xenon or Argon.

Subjects with a history of prior treatment with Xenon and Argon within 6 weeks.

Subjects who have received any of the following interventions within the prescribed period before starting treatment:

investigational drugs within the previous 30 days.

monoamine oxidase inhibitors within the previous fourteen days.

long-acting phenothiazines within the previous six weeks.

other psychotropic drugs within the previous seven days, unless otherwise permitted.

Subjects with any organic or systemic disease or patients who require a therapeutic intervention, not otherwise specified, which would confound the evaluation of the safety of the study medication.

Subjects who reside in a remote geographical area or who do not have regular access to transportation to the clinical facility.

At the completion of the study

Xenon/Argon/Oxygen inhalations was superior to placebo in the acute treatment of global autism.

Xenon/Argon/Oxygen inhalation was superior to placebo in improving functional ability.

Xenon/Argon/Oxygen inhalations was superior to placebo in improving language function.

Xenon/Argon/Oxygen inhalations was superior to placebo improving irritable and hyperactive behavior.

Xenon/Argon/Oxygen inhalations was superior to placebo in improving social deficits.

Example 2

Suppression of Alzheimer's Peptide Induced Monocyte TNF-Alpha Production by Xenon Gas 10 ml of heparinized blood was extracted from healthy volunteers and peripheral blood mononuclear cells were isolated by centrifugation over a ficoll gradient. Cells were subsequently washed in 2× volume phosphate buffered saline, and resuspended in RPMI media supplemented with 10% fetal calf serum. Cells were incubated at a concentration of 10 million cells per ml in 6-well plates in a volume of 2 ml per well. Cells were cultured for 24 hours at 37 Celsius in a fully humidified atmosphere with 5% CO2, subsequent to which non-adherent cells were removed by washing with PBS. Adherent cells were subsequently divided into 2 plates, one plate incubated at normoxic tissue culture, the second plate cultured for 1 hour in 30% xenon by volume, and the third tissue cultured for 2 hours in 30% volume. Cells were treated with control media, 1 ug/ml LPS and 10 µM of amyloid beta peptide Aβ (1-42) for 24 h. Supernatant was collected and assessed for TNF-alpha production by ELISA. As seen in FIG. 1, suppression of induced TNF-alpha production was observed in response incubation with xenon gas.

Example 3

Suppression of Alzheimer's Peptide Induced Dendritic Cell IL-12 Production by Xenon Gas Monocytes from adherent PBMC were isolated as described in Example 1. Dendritic cells were generated by 7 day culture in IL-4 (10 ng/ml) and GM-CSF (20 ng/ml). Media was changed every two days. On day 7, purification of CD1c dendritic cells was performed and cells were cultured in control media, 1 ug/ml LPS and 10 µM of amyloid beta peptide Aβ (1-42) for 24 h. Supernatant was collected and assessed for IL-12 production by ELISA. As seen in FIG. 2, suppression of induced IL-12 production was observed in response incubation with xenon gas.

REFERENCES

1. Stubbs, E. G. and M. L. Crawford, *Depressed lymphocyte responsiveness in autistic children.* J Autism Child Schizophr, 1977. 7(1): p. 49-55.
2. Warren, R. P., et al., *Immune abnormalities in patients with autism.* J Autism Dev Disord, 1986. 16(2): p. 189-97.
3. Yonk, L. J., et al., *CD4+ helper T cell depression in autism.* Immunol Lett, 1990. 25(4): p. 341-5.
4. Vojdani, A., et al., *Low natural killer cell cytotoxic activity in autism: the role of glutathione, IL-2 and IL-15.* J Neuroimmunol, 2008. 205(1-2): p. 148-54.
5. Aarnisalo, J., et al., *Reduced CD4+ T cell activation in children with type 1 diabetes carrying the PTPN22/Lyp 620Trp variant.* J Autoimmun, 2008. 31(1): p. 13-21.
6. Michalski, J. P. and C. McCombs, *Decreased lymphocyte reactivity to a suboptimal concentration of phytohemagglutinin in Sjogren's syndrome.* Arthritis Rheum, 1977. 20(3): p. 851-8.
7. Ichikawa, Y., et al., *Defective expression of OKT4 antigen on the cell surface of helper T lymphocytes in a patient with systemic lupus erythematosus.* Clin Exp Rheumatol, 1983. 1(4): p. 299-305.
8. Nouri, A. M. and G. S. Panayi, *Cytokines and the chronic inflammation of rheumatic disease. III. Deficient interleukin-2 production in rheumatoid arthritis is not due to suppressor mechanisms.* J Rheumatol, 1987. 14(5): p. 902-6.
9. Kitas, G. D., et al., *Deficient interleukin 2 production in rheumatoid arthritis: association with active disease and systemic complications.* Clin Exp Immunol, 1988. 73(2): p. 242-9.
10. Prud'homme, G. J., et al., *Immune dysfunction in diabetes-prone BB rats. Interleukin 2 production and other mitogen-induced responses are suppressed by activated macrophages.* J Exp Med, 1984. 159(2): p. 463-78.
11. Kawase, Y., et al., [*Cellular immune dysfunction in the NOD mouse: suppression of concanavalin A-induced responses in spleen cells by activated macrophages*]. Nihon Naibunpi Gakkai Zasshi, 1989. 65(7): p. 674-85.
12. Zipris, D., et al., *Defective thymic T cell activation by concanavalin A and anti-CD3 in autoimmune nonobese diabetic mice. Evidence for thymic T cell anergy that correlates with the onset of insulitis.* J Immunol, 1991. 146(11): p. 3763-71.

13. Heuer, L., et al., *Reduced levels of immunoglobulin in children with autism correlates with behavioral symptoms*. Autism Res, 2008. 1(5): p. 275-83.
14. Heuer, L. S., et al., *Decreased levels of total immunoglobulin in children with autism are not a result of B cell dysfunction*. J Neuroimmunol, 2012. 251(1-2): p. 94-102.
15. Talaei, N., et al., *T cell and dendritic cell abnormalities synergize to expand pro-inflammatory T cell subsets leading to fatal autoimmunity in B6.NZBc1 lupus-prone mice*. PLoS One, 2013. 8(9): p. e75166.
16. Parietti, V., et al., *Function of CD4+, CD25+ Treg cells in MRL/lpr mice is compromised by intrinsic defects in antigen-presenting cells and effector T cells*. Arthritis Rheum, 2008. 58(6): p. 1751-61.
17. Marleau, A. M., K. L. Summers, and B. Singh, *Differential contributions of APC subsets to T cell activation in nonobese diabetic mice*. J Immunol, 2008. 180(8): p. 5235-49.
18. Grigorenko, E. L., et al., *Macrophage migration inhibitory factor and autism spectrum disorders*. Pediatrics, 2008. 122(2): p. e438-45.
19. Jyonouchi, H., et al., *Impact of innate immunity in a subset of children with autism spectrum disorders: a case control study*. J Neuroinflammation, 2008. 5: p. 52.
20. Volchenkov, R., et al., *Type 1 regulatory T cells and regulatory B cells induced by tolerogenic dendritic cells*. Scand J Immunol, 2013. 77(4): p. 246-54.
21. Martin-Gayo, E., et al., *Plasmacytoid dendritic cells resident in human thymus drive natural Treg cell development*. Blood, 2010. 115(26): p. 5366-75.
22. Amodio, G. and S. Gregori, *Human tolerogenic DC-10: perspectives for clinical applications*. Transplant Res, 2012. 1(1): p. 14.
23. Kleinewietfeld, M. and D. A. Hafler, *Regulatory T cells in autoimmune neuroinflammation*. Immunol Rev, 2014. 259(1): p. 231-44.
24. Bettini, M. and D. A. Vignali, *Regulatory T cells and inhibitory cytokines in autoimmunity*. Curr Opin Immunol, 2009. 21(6): p. 612-8.
25. Silva, S. C., et al., *Autoantibody repertoires to brain tissue in autism nuclear families*. J Neuroimmunol, 2004. 152(1-2): p. 176-82.
26. Vojdani, A., et al., *Immune response to dietary proteins, gliadin and cerebellar peptides in children with autism*. Nutr Neurosci, 2004. 7(3): p. 151-61.
27. Cabanlit, M., et al., *Brain-specific autoantibodies in the plasma of subjects with autistic spectrum disorder*. Ann N Y Acad Sci, 2007. 1107: p. 92-103.
28. Singh, V. K., *Plasma increase of interleukin-12 and interferon-gamma. Pathological significance in autism*. J Neuroimmunol, 1996. 66(1-2): p. 143-5.
29. Al-Ayadhi, L. Y., *Pro-inflammatory cytokines in autistic children in central Saudi Arabia*. Neurosciences (Riyadh), 2005. 10(2): p. 155-8.
30. Ashwood, P., et al., *Elevated plasma cytokines in autism spectrum disorders provide evidence of immune dysfunction and are associated with impaired behavioral outcome*. Brain Behav Immun, 2011. 25(1): p. 40-5.
31. Al-Ayadhi, L. Y. and G. A. Mostafa, *Elevated serum levels of interleukin-17A in children with autism*. J Neuroinflammation, 2012. 9: p. 158.
32. D'Addio, F., et al., *The link between the PDL1 costimulatory pathway and Th17 in fetomaternal tolerance*. J Immunol, 2011. 187(9): p. 4530-41.
33. Kucuksezer, U. C., et al., *Triggering of specific Toll-like receptors and proinflammatory cytokines breaks allergen-specific T-cell tolerance in human tonsils and peripheral blood*. J Allergy Clin Immunol, 2013. 131(3): p. 875-85.
34. Burkett, P. R., G. Meyer Zu Horste, and V. K. Kuchroo, *Pouring fuel on the fire: Th17 cells, the environment, and autoimmunity*. J Clin Invest, 2015: p. 1-9.
35. Liang, Y., H. F. Pan, and D. Q. Ye, *IL-17A-producing CD8(+)T cells as therapeutic targets in autoimmunity*. Expert Opin Ther Targets, 2015. 19(5): p. 651-61.
36. Shabgah, A. G., E. Fattahi, and F. Z. Shahneh, *Interleukin-17 in human inflammatory diseases*. Postepy Dermatol Alergol, 2014. 31(4): p. 256-61.
37. Li, D., et al., *Interleukin-17 in systemic lupus erythematosus: A comprehensive review*. Autoimmunity, 2015: p. 1-9.
38. Schaffert, H., et al., *IL-17-producing CD4(+) T cells contribute to the loss of B-cell tolerance in experimental autoimmune myasthenia gravis*. Eur J Immunol, 2015. 45(5): p. 1339-47.
39. Reinert-Hartwall, L., et al., *Th1/Th17 plasticity is a marker of advanced beta cell autoimmunity and impaired glucose tolerance in humans*. J Immunol, 2015. 194(1): p. 68-75.
40. Abe, M., Y. Hiasa, and M. Onji, *T helper 17 cells in autoimmune liver diseases*. Clin Dev Immunol, 2013: p. 607073.
41. Blardi, P., et al., *Variations of plasma leptin and adiponectin levels in autistic patients*. Neurosci Lett, 2010. 479(1): p. 54-7.
42. Suzuki, K., et al., *Plasma cytokine profiles in subjects with high-functioning autism spectrum disorders*. PLoS One, 2011. 6(5): p. e20470.
43. Masi, A., et al., *Cytokine aberrations in autism spectrum disorder: a systematic review and meta-analysis*. Mol Psychiatry, 2015. 20(4): p. 440-6.
44. Ashwood, P., et al., *Associations of impaired behaviors with elevated plasma chemokines in autism spectrum disorders*. J Neuroimmunol, 2011. 232(1-2): p. 196-9.
45. Emanuele, E., et al., *Increased serum levels of high mobility group box 1 protein in patients with autistic disorder*. Prog Neuropsychopharmacol Biol Psychiatry, 2010. 34(4): p. 681-3.
46. Ashwood, P., et al., *Decreased transforming growth factor beta1 in autism: a potential link between immune dysregulation and impairment in clinical behavioral outcomes*. J Neuroimmunol, 2008. 204(1-2): p. 149-53.
47. Sweeten, T. L., D. J. Posey, and C. J. McDougle, *High blood monocyte counts and neopterin levels in children with autistic disorder*. Am J Psychiatry, 2003. 160(9): p. 1691-3.
48. Sweeten, T. L., et al., *High nitric oxide production in autistic disorder: a possible role for interferon-gamma*. Biol Psychiatry, 2004. 55(4): p. 434-7.
49. Zhao, H. X., S. S. Yin, and J. G. Fan, *High plasma neopterin levels in Chinese children with autism spectrum disorders*. Int J Dev Neurosci, 2015. 41: p. 92-7.
50. Messahel, S., et al., *Urinary levels of neopterin and biopterin in autism*. Neurosci Lett, 1998. 241(1): p. 17-20.
51. Enstrom, A. M., et al., *Differential monocyte responses to TLR ligands in children with autism spectrum disorders*. Brain Behav Immun, 2010. 24(1): p. 64-71.
52. Ashwood, P., et al., *Altered T cell responses in children with autism*. Brain Behav Immun, 2011. 25(5): p. 840-9.
53. Korvatska, E., et al., *Genetic and immunologic considerations in autism*. Neurobiol Dis, 2002. 9(2): p. 107-25.
54. Malek-Ahmadi, P., *Cytokines and etiopathogenesis of pervasive developmental disorders*. Med Hypotheses, 2001. 56(3): p. 321-4.

55. Boris, M., et al., *Effect of pioglitazone treatment on behavioral symptoms in autistic children.* J Neuroinflammation, 2007. 4: p. 3.
56. Akhondzadeh, S., et al., *Double-blind placebo-controlled trial of pentoxifylline added to risperidone: effects on aberrant behavior in children with autism.* Prog Neuropsychopharmacol Biol Psychiatry, 2010. 34(1): p. 32-6.
57. Gupta, S., D. Samra, and S. Agrawal, *Adaptive and Innate Immune Responses in Autism: Rationale for Therapeutic Use of Intravenous Immunoglobulin.* J Clin Immunol, 2010.
58. Golla, S. and J. A. Sweeney, *Corticosteroid therapy in regressive autism: Preliminary findings from a retrospective study.* BMC Med, 2014. 12: p. 79.
59. Warren, R. P., et al., *Immunogenetic studies in autism and related disorders.* Mol Chem Neuropathol, 1996. 28(1-3): p. 77-81.
60. Torres, A. R., A. Maciulis, and D. Odell, *The association of MHC genes with autism.* Front Biosci, 2001. 6: p. D936-43.
61. Sweeten, T. L., et al., *Increased prevalence of familial autoimmunity in probands with pervasive developmental disorders.* Pediatrics, 2003. 112(5): p. e420.
62. Torres, A. R., et al., *The association and linkage of the HLA-A2 class I allele with autism.* Hum Immunol, 2006. 67(4-5): p. 346-51.
63. Lee, L. C., et al., *HLA-DR4 in families with autism.* Pediatr Neurol, 2006. 35(5): p. 303-7.
64. Jung, J. Y., I. S. Kohane, and D. P. Wall, *Identification of autoimmune gene signatures in autism.* Transl Psychiatry, 2011. 1: p. e63.
65. Chien, Y. L., et al., *Association of HLA-DRB1 alleles and neuropsychological function in autism.* Psychiatr Genet, 2012. 22(1): p. 46-9.
66. Ramos, P. S., et al., *Immune function genes CD99L2, JARID2 and TPO show association with autism spectrum disorder.* Mol Autism, 2012. 3(1): p. 4.
67. Needleman, L. A. and A. K. McAllister, *The major histocompatibility complex and autism spectrum disorder.* Dev Neurobiol, 2012. 72(10): p. 1288-301.
68. Tones, A. R., J. B. Westover, and A. J. Rosenspire, *HLA Immune Function Genes in Autism.* Autism Res Treat, 2012. 2012: p. 959073.
69. Guerini, F. R., et al., *An HLA-G(*)14bp insertion/deletion polymorphism associates with the development of autistic spectrum disorders.* Brain Behav Immun, 2015. 44: p. 207-12.
70. Careaga, M. and P. Ashwood, *Autism spectrum disorders: from immunity to behavior.* Methods Mol Biol, 2012. 934: p. 219-40.
71. Onore, C., M. Careaga, and P. Ashwood, *The role of immune dysfunction in the pathophysiology of autism.* Brain Behav Immun, 2012. 26(3): p. 383-92.
72. Singh, V. K., *Phenotypic expression of autoimmune autistic disorder (AAD): a major subset of autism.* Ann Clin Psychiatry, 2009. 21(3): p. 148-61.
73. Theoharides, T. C., D. Kempuraj, and L. Redwood, *Autism: an emerging 'neuroimmune disorder' in search of therapy.* Expert Opin Pharmacother, 2009. 10(13): p. 2127-43.
74. Enstrom, A. M., J. A. Van de Water, and P. Ashwood, *Autoimmunity in autism.* Curr Opin Investig Drugs, 2009. 10(5): p. 463-73.
75. Castellani, M. L., et al., *Autism and immunity: revisited study.* Int J Immunopathol Pharmacol, 2009. 22(1): p. 15-9.
76. Pardo, C. A., D. L. Vargas, and A. W. Zimmerman, *Immunity, neuroglia and neuroinflammation in autism.* Int Rev Psychiatry, 2005. 17(6): p. 485-95.
77. Smith, T. C., et al., *New onset and persistent symptoms of post-traumatic stress disorder self reported after deployment and combat exposures: prospective population based US military cohort study.* BMJ, 2008. 336 (7640): p. 366-71.
78. Daugirdaite, V., O. van den Akker, and S. Purewal, *Posttraumatic stress and posttraumatic stress disorder after termination of pregnancy and reproductive loss: a systematic review.* J Pregnancy, 2015. 2015: p. 646345.
79. Foa, E. B., et al., *Social, psychological, and psychiatric interventions following terrorist attacks: recommendations for practice and research.* Neuropsychopharmacology, 2005. 30(10): p. 1806-17.
80. Chen, L. P., et al., *Sexual abuse and lifetime diagnosis of psychiatric disorders: systematic review and meta-analysis.* Mayo Clin Proc, 2010. 85(7): p. 618-29.
81. Jenkins, M. A., et al., *Learning and memory in rape victims with posttraumatic stress disorder.* Am J Psychiatry, 1998. 155(2): p. 278-9.
82. Bremner, J. D., et al., *Deficits in short-term memory in adult survivors of childhood abuse.* Psychiatry Res, 1995. 59(1-2): p. 97-107.
83. Yehuda, R., *Biology of posttraumatic stress disorder.* J Clin Psychiatry, 2001. 62 Suppl 17: p. 41-6.
84. Bremner, J. D., *The relationship between cognitive and brain changes in posttraumatic stress disorder.* Ann N Y Acad Sci, 2006. 1071: p. 80-6.
85. Bremner, J. D., et al., *MRI-based measurement of hippocampal volume in patients with combat-related posttraumatic stress disorder.* Am J Psychiatry, 1995. 152(7): p. 973-81.
86. Gurvits, T. V., et al., *Magnetic resonance imaging study of hippocampal volume in chronic, combat-related posttraumatic stress disorder.* Biol Psychiatry, 1996. 40(11): p. 1091-9.
87. Bremner, J. D., et al., *Magnetic resonance imaging-based measurement of hippocampal volume in posttraumatic stress disorder related to childhood physical and sexual abuse—a preliminary report.* Biol Psychiatry, 1997. 41(1): p. 23-32.
88. Purgato, M., et al., *Paroxetine versus other anti-depressive agents for depression.* Cochrane Database Syst Rev, 2014. 4: p. CD006531.
89. Marshall, R. D., et al., *Efficacy and safety of paroxetine treatment for chronic PTSD: a fixed-dose, placebo-controlled study.* Am J Psychiatry, 2001. 158(12): p. 1982-8.
90. Marshall, R. D., et al., *A controlled trial of paroxetine for chronic PTSD, dissociation, and interpersonal problems in mostly minority adults.* Depress Anxiety, 2007. 24(2): p. 77-84.
91. Davidson, J. R., *Pharmacologic treatment of acute and chronic stress following trauma:* 2006. J Clin Psychiatry, 2006. 67 Suppl 2: p. 34-9.
92. Vermetten, E., et al., *Alterations in stress reactivity after long-term treatment with paroxetine in women with post-traumatic stress disorder.* Ann N Y Acad Sci, 2006. 1071: p. 184-202.
93. Kucukalic, A., A. Bravo-Mehmedbasic, and A. Dzubur-Kulenovic, *Paroxetine in the treatment of post traumatic stress disorder: our experiences.* Bosn J Basic Med Sci, 2008. 8(1): p. 76-9.
94. Jones, K. A. and C. Thomsen, *The role of the innate immune system in psychiatric disorders.* Mol Cell Neurosci, 2013. 53: p. 52-62.

95. Acosta, S. A., et al., *Influence of post-traumatic stress disorder on neuroinflammation and cell proliferation in a rat model of traumatic brain injury.* PLoS One, 2013. 8(12): p. e81585.
96. Jones, M. E., et al., *The role of brain interleukin-1 in stress-enhanced fear learning.* Neuropsychopharmacology, 2015. 40(5): p. 1289-96.
97. Gola, H., et al., *Posttraumatic stress disorder is associated with an enhanced spontaneous production of pro-inflammatory cytokines by peripheral blood mononuclear cells.* BMC Psychiatry, 2013. 13: p. 40.
98. Oganesyan, L. P., et al., *Classic and alternative complement cascades in post-traumatic stress disorder.* Bull Exp Biol Med, 2009. 148(6): p. 859-61.
99. Levkovitz, Y., et al., *Early post-stressor intervention with minocycline, a second-generation tetracycline, attenuates post-traumatic stress response in an animal model of PTSD.* Eur Neuropsychopharmacol, 2015. 25(1): p. 124-32.
100. Sofuoglu, M., R. Rosenheck, and I. Petrakis, *Pharmacological treatment of comorbid PTSD and substance use disorder: recent progress.* Addict Behav, 2014. 39(2): p. 428-33.
101. David, H. N., et al., *Argon prevents the development of locomotor sensitization to amphetamine and amphetamine-induced changes in mu opioid receptor in the nucleus accumbens.* Med Gas Res, 2014. 4(1): p. 21.
102. David, H. N., et al., *Reduction of ischemic brain damage by nitrous oxide and xenon.* J Cereb Blood Flow Metab, 2003. 23(10): p. 1168-73.
103. David, H. N., et al., *Neuroprotective effects of xenon: a therapeutic window of opportunity in rats subjected to transient cerebral ischemia.* FASEB J, 2008. 22(4): p. 1275-86.
104. David, H. N., et al., *Ex vivo and in vivo neuroprotection induced by argon when given after an excitotoxic or ischemic insult.* PLoS One, 2012. 7(2): p. e30934.
105. Bubeev Iu, A., A. S. Kal'manov, and T. I. Kotrovskaia, [*Correction of the functional state of deck aviation pilots by the course of inhalation of therapeutic doses of xenon during long march*]. Aviakosm Ekolog Med, 2011. 45(4): p. 10-5.
106. Kochanek, P. M. and T. C. Jackson, *Will the next breakthrough for neuroprotection after cardiac arrest come out of thin air?* Shock, 2014. 41(1): p. 85-6.
107. Laitio, R., et al., *Effect of Inhaled Xenon on Cerebral White Matter Damage in Comatose Survivors of Out-of-Hospital Cardiac Arrest: A Randomized Clinical Trial.* JAMA, 2016. 315(11): p. 1120-8.
108. Arola, O. J., et al., *Feasibility and cardiac safety of inhaled xenon in combination with therapeutic hypothermia following out-of-hospital cardiac arrest.* Crit Care Med, 2013. 41(9): p. 2116-24.
109. Azzopardi, D., et al., *Moderate hypothermia within 6 h of birth plus inhaled xenon versus moderate hypothermia alone after birth asphyxia (TOBY-Xe): a proof-of-concept, open-label, randomised controlled trial.* Lancet Neurol, 2015.
110. Britton, G. L., et al., *In vivo therapeutic gas delivery for neuroprotection with echogenic liposomes.* Circulation, 2010. 122(16): p. 1578-87.
111. Peng, T., et al., *Therapeutic time window and dose dependence of xenon delivered via echogenic liposomes for neuroprotection in stroke.* CNS Neurosci Ther, 2013. 19(10): p. 773-84.
112. Maze, M., *Preclinical neuroprotective actions of xenon and possible implications for human therapeutics: a narrative review.* Can J Anaesth, 2016. 63(2): p. 212-26.
113. Sanders, R. D. and M. Maze, *Xenon: from stranger to guardian.* Curr Opin Anaesthesiol, 2005. 18(4): p. 405-11.
114. Esencan, E., et al., *XENON in medical area: emphasis on neuroprotection in hypoxia and anesthesia.* Med Gas Res, 2013. 3(1): p. 4.

The invention claimed is:
1. A method of treating an autism spectrum disorder comprising the steps of: a) identifying a patient with an autism spectrum disorder; and b) administering a noble gas containing composition comprising oxygen and/or air and a proportion by volume of 20 to 70% of a noble gas at a sufficient concentration and frequency to a patient in need thereof to effectively treat said autism spectrum disorder.
2. The method of claim 1, wherein said noble gas is xenon and/or a xenon donor.
3. The method of claim 1, wherein said noble gas containing composition comprises a 25% xenon and a 75% air mixture by volume.
4. The method of claim 1, wherein the noble gas is xenon gas and said administration is performed at a volume of 10 liters of the noble gas composition per administration, and at 3 administrations per week.

\* \* \* \* \*